United States Patent [19]
Vasile

[11] 4,307,616
[45] Dec. 29, 1981

[54] SIGNAL PROCESSING TECHNIQUE FOR ULTRASONIC INSPECTION

[75] Inventor: Carmine F. Vasile, Huntington, N.Y.

[73] Assignee: Rockwell International Corporation, El Segundo, Calif.

[21] Appl. No.: 106,994

[22] Filed: Dec. 26, 1979

[51] Int. Cl.³ .............................................. G01N 29/04
[52] U.S. Cl. ......................................... 73/643; 73/620
[58] Field of Search ................ 73/602, 643, 609, 610, 73/618, 620

[56] References Cited

U.S. PATENT DOCUMENTS

| | | |
|---|---|---|
| 3,850,028 | 11/1974 | Thompson et al. .................. 73/643 |
| 4,104,922 | 8/1978 | Alers et al. ............................. 73/643 |
| 4,127,035 | 11/1978 | Vasile .................................... 73/643 |
| 4,184,374 | 1/1980 | Thompson et al. ................... 73/643 |

*Primary Examiner*—Stephen A. Kreitman
*Attorney, Agent, or Firm*—H. Fredrick Hamann; Craig O. Malin; John J. Deinken

[57] ABSTRACT

Disclosed is a correlation receiver for processing an elctrical signal derived from an acoustic signal in a test object, including a signal generator for producing a reference waveform, a multiplier for combining the electrical signal and the reference waveform, an inegrator for integrating the combined signal, and a sample and hold circuit for detecting and holding the output of the integrator. In another embodiment, the signal generator also produces a second reference waveform in quadrature with the first reference waveform, and the receiver further inclues a second multiplier for combining the electrical signal and the second reference waveform, a second integrator for integrating the combined signal, and a means for combining the integrated first and second combined signals to produce an output indicating the structural integrity of the test object.

13 Claims, 5 Drawing Figures

SIGNAL PROCESSING TECHNIQUE FOR ULTRASONIC INSPECTION

GOVERNMENT RIGHTS

The invention described herein was made in the course of or under a contract with the U.S. Army.

BACKGROUND OF THE INVENTION

This invention relates to signal processing techniques and, more particularly, to the processing of an electrical signal derived from an acoustic signal generated in a test object.

The electromagnetic acoustic transducer (EMAT) is a recently developed device which has generated particular interest in the field of nondestructive evaluation because an EMAT may be operated in a noncontact mode, thereby enabling a high rate of ultrasonic inspection to be achieved with an attendant reduction in the costs of quality control. The noncontact feature of such a transducer is a consequence of the basic principles of operation of an EMAT, which depend upn the interactions between a magnetic field and an alternating current. When a conductor carrying a dynamic current is placed adjacent to a metallic object, eddy currents are induced within the object by the electromagnetic forces associated with the current. If, in addition, a static magnetic field is superimposed in the object, the induced eddy currents will be subjected to a force which can generate an acoustic wave in the object. Conversely, if the material in the object is set in motion due to a propagating acoustic wave, eddy currents will be induced in the metal as the wave travels through the magnetic field. These currents may be inductively detected by a similarly placed conductor associated with an electronic receiver. In ferromagnetic metals, an additional transduction mechanism due to magnetostriction can significantly increase the transducer efficiency.

EMATs can be configured to excite various forms of acoustic waves, such as surface waves, bulk shear waves, angle shear waves, and angle longitudinal waves. Some representative electromagnetic acoustic transducer structures, for example, are disclosed in U.S. Pat. Nos. 4,127,035, 4,104,922, and 3,850,028. These unique features have prompted the use of EMATs in ultrasonic inspection systems for detecting a number of different kinds of defects, including such flaws as cracks, surface abnormalities, weld defects, and corrosion-induced pitting and wall thinning. In one illustrative application, for example, EMATs have been employed in a system to measure the characteristics of an ultrasonic signal propagated through a defective region of a pipeline. Some characteristic properties of the EMAT, however, such as its inherently low level of signal generation, have led to undesirable consequences. These conventional systems, for example, tend to be excessively sensitive to local inhomogeneties in the pipe. Additional deficiencies with such systems include the presence of excessive levels of random electronic noise, impulsive noise produced by electronic machinery, and grain noise arising from the material being tested.

Consequently, a need has developed in the art for an improved technique for processing signals from an EMAT-equipped ultrasonic testing system.

SUMMARY OF THE INVENTION

It is a general object of this invention to provide a novel method and apparatus for processing an electrical signal derived from an acoustical signal in a test object.

A correlation receiver for processing an electrical signal, according to the present invention, includes a signal generator for producing a reference waveform, a multiplier for combining the electrical signal and the reference waveform, and an integrator for integrating the combined signal.

In a more particular embodiment, the receiver further includes a delay circuit for delaying the reference waveform so that the waveform and the electrical signal are applied to the multiplier simultaneously.

In another embodiment, a correlation receiver for processing an electrical signal derived from an acoustical signal in a test object, according to this invention, includes a signal generator for producing a first reference waveform and a second reference waveform in quadrature with the first waveform, a first multiplier for combining the electrical signal and the first reference waveform, a second multiplier for combining the electrical signal and the second reference waveform, a first integrator for integrating the first combined signal, and a means for combining the integrated first and second combined signals to produce an output indicating the structural integrity of the test object.

In a more particular embodiment, the receiver may further include a first sample and hold circuit for detecting and holding the output of the first integrator, a second sample and hold circuit for detecting and holding the output of the second integrator, a first analog to digital converter for digitizing the output of the first sample and hold circuit, and a second analog to digital converter for digitizing the output of the second sample and hold circuit. In addition, the receiver may further include a central data and control processor for timing the output of the first and second reference waveforms from the generator, initiating the digitization of the sample and hold outputs, making an acceptance decision regarding the test object based on the output of the combining means, and resetting the receiver.

An apparatus for evaluating the structural integrity of an object, according to the present invention, includes a signal generator for producing an input signal and a reference waveform, an input transducer for receiving the input signal and generating an acoustic signal in the object, an output transducer for detecting the acoustic signal and generating an electrical output signal responsive thereto, a multiplier for combining the electrical output signal and the reference waveform, and an integrator for integrating the combined signal.

In an alternative embodiment, an apparatus for evaluating the structural integrity of an object, according to the present invention, includes a signal generator for producing an input signal, a first reference waveform, and a second reference waveform, an input transducer for receiving the input signal and generating an acoustic signal in the object, an output transducer for detecting the acoustic signal and generating an electrical output signal responsive thereto, a first multiplier for combining the electrical output signal and the first reference waveform, a second multiplier for combining the electrical output signal and the second reference waveforms, a first integrator for integrating the first combined signal, a second integrator for integrating the second combined signal, and a means for combining the integrated signals to produce an output indicating the structural integrity of the test object.

A method of time domain correlating an electrical signal derived from an acoustic signal in a test object, according to the present invention, includes the steps of:
(a) generating a first reference waveform,
(b) combining the electrical signal and the reference waveform, and
(c) integrating the product of the multiplication.

In a more particular embodiment, the method further includes the steps of:
(d) generating a second reference waveform in quadrature with the first waveform,
(e) combining the electrical signal and the second reference waveform by multiplication,
(f) integrating the product of the multiplication, and
(g) combining the integrands from steps (c) and (f) to provide an output indicating the structural integrity of the test object.

These examples of the more important features of the invention have been broadly outlined in order to facilitate an understanding of the detailed description which follows and so that the contributions which this invention provides to the art may be better appreciated. There are, of course, additional features of the invention which will be further described below and which are included within the subject matter of the appended claims.

BRIEF DESCRIPTION OF THE DRAWINGS

Additional objects, features, and advantages of the present invention will become apparent by referring to the detailed description of the preferred embodiments in connection with the accompanying drawings wherein the same reference numerals refer to like elements throughout all the figures. In the drawings.

DESCRIPTION OF THE PREFERRED EMBODIMENTS

Figure 1:
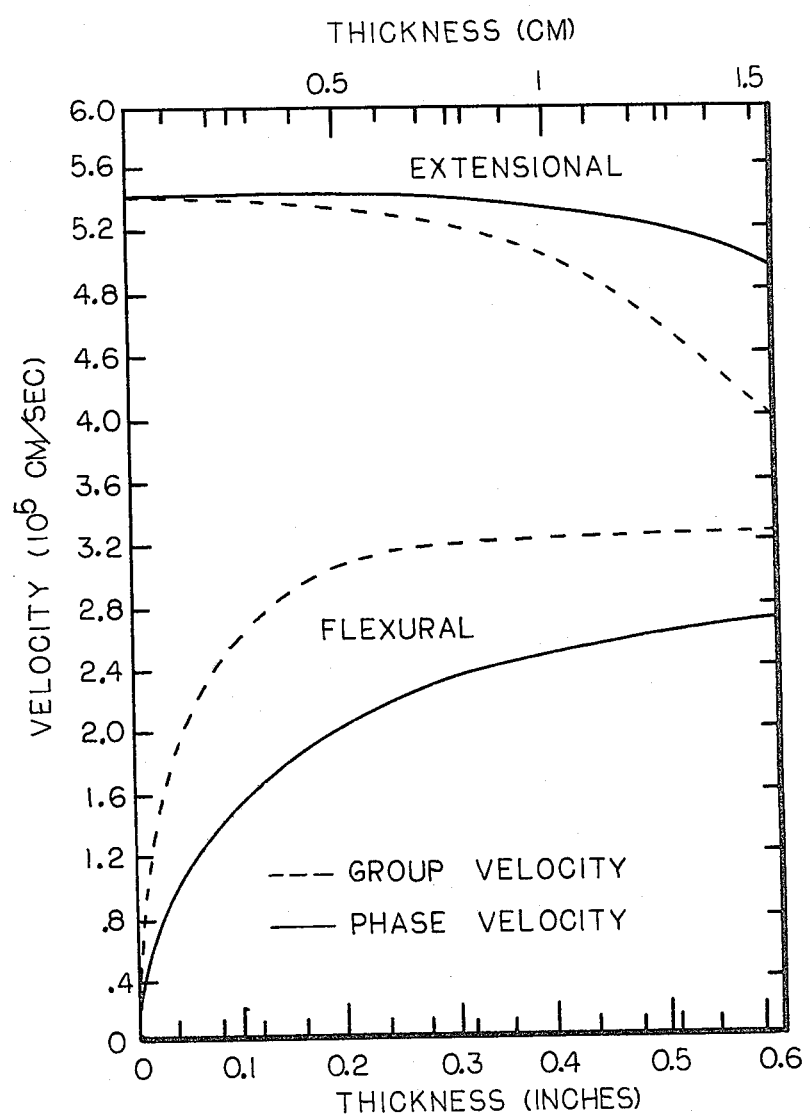
FIG. 1 is a plot of the phase and group velocities of fast and slow Lamb waves at 130 KHz in a steel plate, as a function of the thickness of the plate.

One particular embodiment of the present invention has been employed in an apparatus for making an ultrasonic measurement of the thickness of a plate material, such as the wall of a pipeline. The velocity versus thickness plot of FIG. 1 indicates how the velocity of propagation of both fast (extensional) and slow (flexural) Lamb waves depends upon the thickness of a steel wall in which the waves are traveling, for the particular case of a 130 KHz wave. Two curves are shown for each wave type because two different arrival times are possible. Thus, if the wave is in the form of a short ultrasonic pulse or tone burst, the arrival time of the total group of individual cycles is controlled by the group velocity, which is shown by the dashed lines. The arrival time of a particular feature or cycle within the pulse, however, is controlled by the phase velocity, indicated by the solid lines. A measurement of the shift in the envelope arrival time for a particular change in the propagation distance will indicate the group velocity, while a measurement of the time shift of a particular cycle within the pulse will yield the phase velocity. In a precision thickness measurement system making use of these shifts, such as would be employed to inspect a pipeline for corrosion thinning, the shift in the arrival time of a particular phase feature within a tone burst can be more accurately detected than the arrival time of the envelope of the total pulse. Thus, the phase velocity is the quantity of interest in this system application and the use of the slow Lamb wave is therefore recommended because its phase velocity exhibits a greater sensitivity to thickness changes.

Unfortunately, however, it is difficult to monitor the arrival time of a particular phase feature (the peak of a particular cycle or a particular zero crossing) in an RF tone burst signal using either conventional electronic circuits or a visual display, since a particular feature within the burst cannot be located without the input of considerable additional information concerning the burst. Systems which merely compare the phase of all the cycles within the burst with a standard signal, for example, are electronically simple but will yield ambiguous results for phase shifts in excess of $2\pi$ radians. The correlation receiver of the present invention, however, is particularly suited to overcoming these problems.

Figure 2:
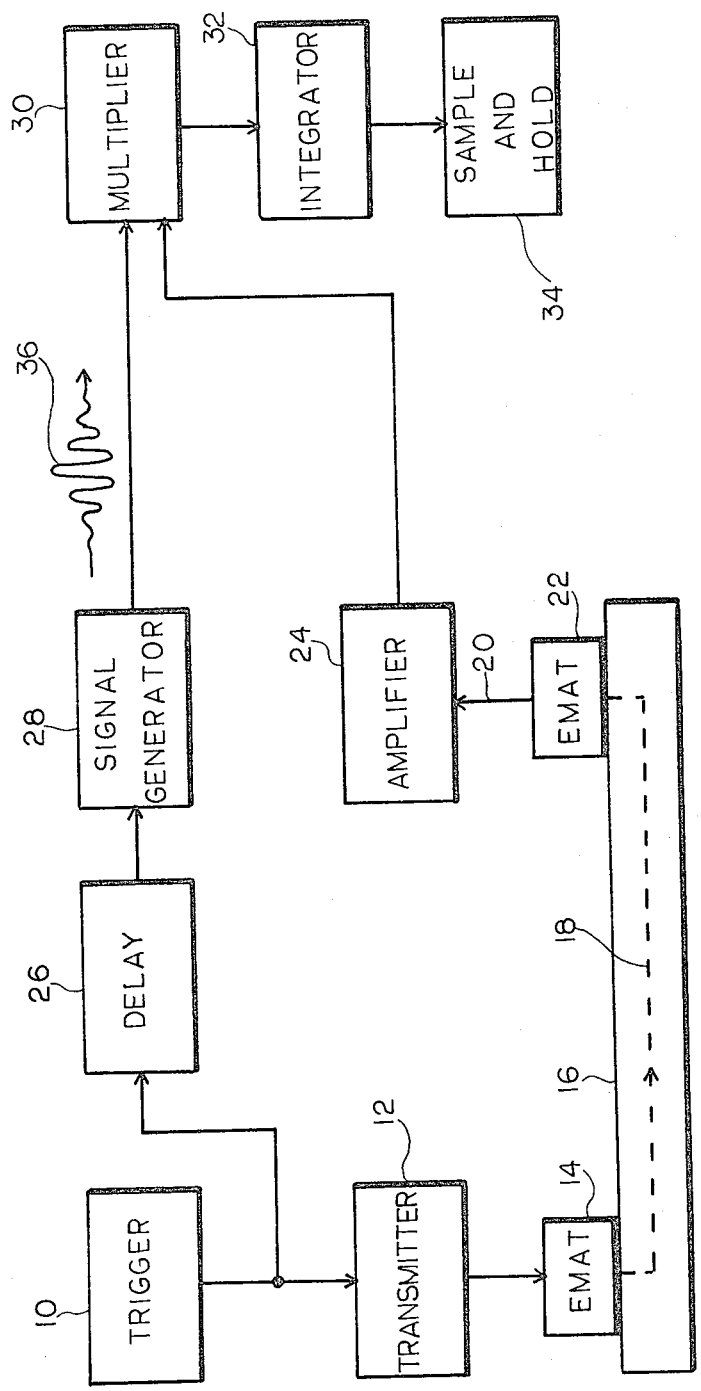
FIG. 2 is a block diagram of an ultrasonic measuring apparatus which incorporates one embodiment of the present invention.

FIG. 2 illustrates, in block diagram form, an ultrasonic thickness measuring apparatus which incorporates one embodiment of a correlation receiver according to the present invention. In this apparatus, a trigger circuit 10 initiates a signal from a pulsed transmitter 12, which in turn drives a transmitting electromagnetic acoustic transducer (EMAT) 14. The EMAT is placed near a metallic test object 16, so that it generates an acoustic signal 18 in the test object. The signal propagates through a portion of the object and induces a corresponding electrical signal 20 in a receiving EMAT 22, the signal then being boosted by an amplifier 24. The correlation receiver in this embodiment consists of the amplifier 24 operating in cooperation with a delay circuit 26, a signal generator 28, a multiplier 30, an integrator 32, and a sample and hold circuit 34.

The initiating pulse from the trigger circuit 10 also is applied to the delay circuit 26 which, after a preselected delay, triggers the signal generator 28 to produce a reference waveform 36. In this manner, the electrical signal 20 and the reference waveform 36 are applied to the multiplier 30 simultaneously. After multiplication, the combined signal is integrated in the integrator 32, the output of which is preserved by the sample and hold circuit 34.

Although the embodiment illustrated in FIG. 2 utilizes a pulsed transmitter to drive the transmitting EMAT and a signal generator to provide the reference waveform, those skilled in the art will appreciated that an alternative arrangement may be utilized in which the signal generator is employed to provide a signal for both the transmitting EMAT and the reference waveform.

The correlation process of this invention operates in the apparatus of FIG. 2 as follows. An acoustic signal $S(t)$, arriving after a delay time determined by the velocity of sound and the path length in the pipe, is multiplied by a reference signal R(t), which is a pulse of the same frequency as S(t), timed by the delay circuit to occur at approximately the same time as S(t). The output, after multiplication and integration, is a voltage whose amplitude is determined by the equation:

$$V = \int_0^T S(t) R(t) \, dt \tag{1}$$

$$= \int_0^T S_o \cos(\omega_o + Q) R_o \cos\omega_o t \, dt$$

$$= \tfrac{1}{2} \cos Q \int_0^T a(t) \, dt$$

where Q is the phase difference between the signal and the reference, a(t) is the envelope function of the signal, and T is the time duration of the signal.

Thus, the output of the correlation receiver is a DC voltage whose amplitude is proportional to the Cosine of th4e phase angle between the reference and the signal. The arrival time $T_a$ of a signal which has passed under a thin region of length W and depth C, and then returned under the thin region before detection, is given by:

$$T_a = \frac{2(D-W)}{V_1} + \frac{2W}{V_2} = \frac{2D}{V_1} + 2W\left[\frac{1}{V_2} - \frac{1}{V_1}\right] \tag{2}$$

where $V_1$ and $V_2$ are the velocities of propagation of the sound wave in the "good" part of the plate, with thickness T, and in the thin part of the plate, with thickness T-C, respectively. Since $2D/V_1$ is the transit time for a "good" region, that time can be used to set the delay time of the reference signal in the correlation receiver, the output of the receiver then being:

$$V = V_o \cos 4\pi f W \left[\frac{1}{V_2} - \frac{1}{V_1}\right] \tag{3}$$

where $V_o$ is determined by the pulse envelope function used in a particular test sequence.

Figure 3:
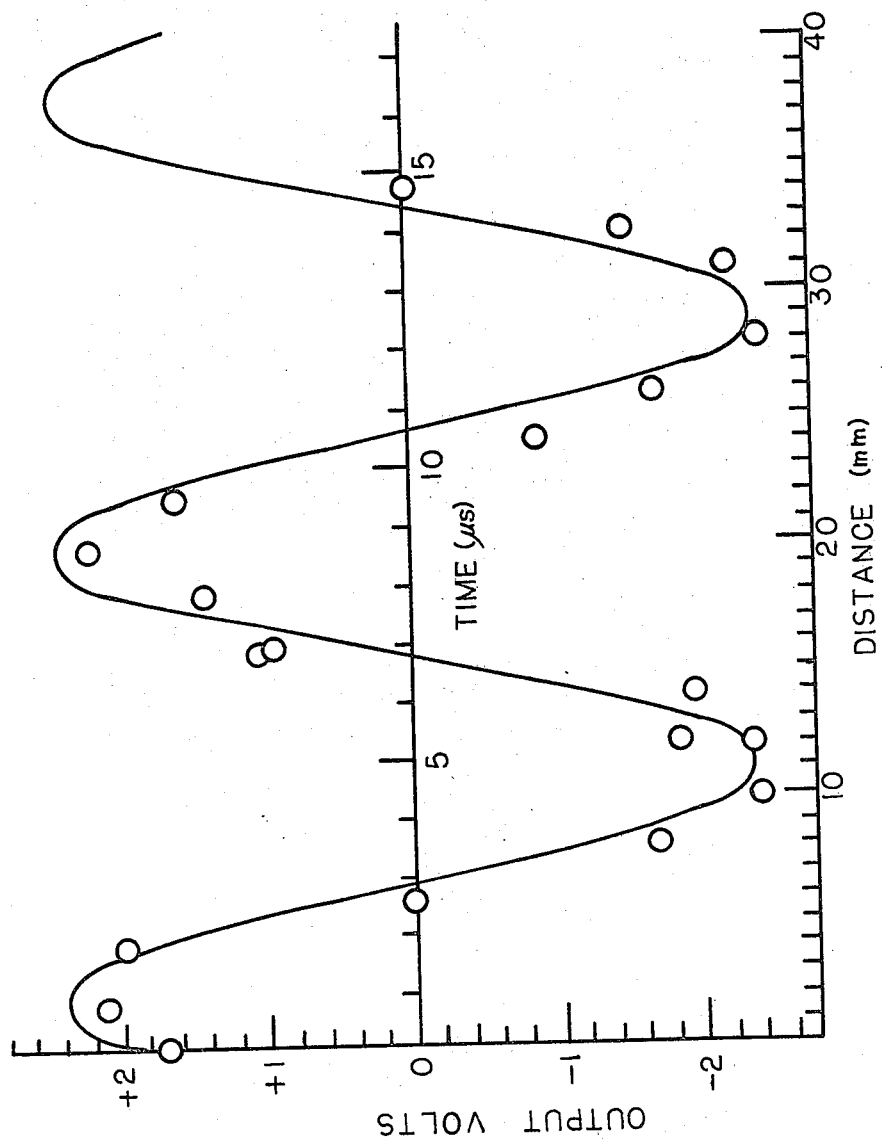
FIG. 3 is a plot illustrating the measured output of the correlation receiver employed in the apparatus of FIG. 2 as a function of the change in acoustic path length between the transmitter and receiver.

The operation of the correlation receiver utilized in the above embodiment of this invention was verified by a series of experiments conducted on a ⅜' thick flat metal plate into which 4 thin regions were machined to depths of 40, 80, 120, and 160 mils, respectively. To demonstrate the operation of the receiver, the transmitter and receiver transducers were moved along a line perpendicular to an edge of the plate. With the receiver detecting the ultrasonic signal reflected from the edge, the time of arrival of the signal shifted as the transducers were moved through thinned regions and the distance of wave travel changed. By carefully measuring the output of the correlation receiver as a function of the change in acoustic path (twice the distance moved), the graph in FIG. 3 was developed, showing a Cosine curve, as expected from Equation 3, with a period of 18 mm. Since the system operated at a frequency of 130 KHz, the 18 mm wavelength implies a phase velocity for the sound waves of $2.34 \times 10^5$ cm/sec, which is in satisfactory agreement with predicted results for the plate used.

The theoretical argument and analysis discussed above with respect to the embodiment of the invention illustrated in FIG. 2 is based on the assumption that the envelope function a(t) remains constant during a measurement. It has been found by experiment, however, that this is not always a valid assumption and can introduce considerable error into some measurements. This source of error can be avoided by the present invention through the use of a second embodiment of the correlation receiver. If the reference function R(t) is chosen to have the form $R_o \sin \omega t$ instead of $R_o \cos \omega t$, Equation 1 will contain Sin Q rather than Cos Q as a term. Thus, if two reference signals in quadrature are supplied in the correlation receiver, the ratio of their outputs will depend only upon Tan Q and will be independent of the envelope function, that is:

$$V = \frac{\tfrac{1}{2} \sin Q \int_0^T a(t) \, dt}{\tfrac{1}{2} \cos Q \int_0^T a(t) \, dt} = \tan Q. \tag{4}$$

An embodiment of the correlation receiver employing this principle has been developed in a prototype machine for accomplishing the ultrasonic inspection of artillery projectiles. In this machine, which is designed to be installed as a part of a production line for manufacturing the shells, a projectile is lifted hydraulically and positioned between the poles of an electromagnet, where a raster of approximately 30 transducers is brought into contact with the projectile. The electromagnet is activated to produce a field of sufficient strength to achieve maximum magnetostrictive enhancement of ultrasonic signals in the projectile. The projectile is then rotated in the magnetic field while the EMAT transducers are sequentially activated to achieve the inspection of substantially the entire area of the projectile. Ultrasonic signals reflected from specific locations within the projectile are received by the transducers and delivered to a central processor where they are compared to accept/reject criteria established for different regions of the projectile. All projectile movement, power requirements, launching of ultrasonic signals, switching of electromagnet coil current, and necessary accept/reject decisions are centrally controlled through the same processor to completely automate the inspection process.

Figure 4:
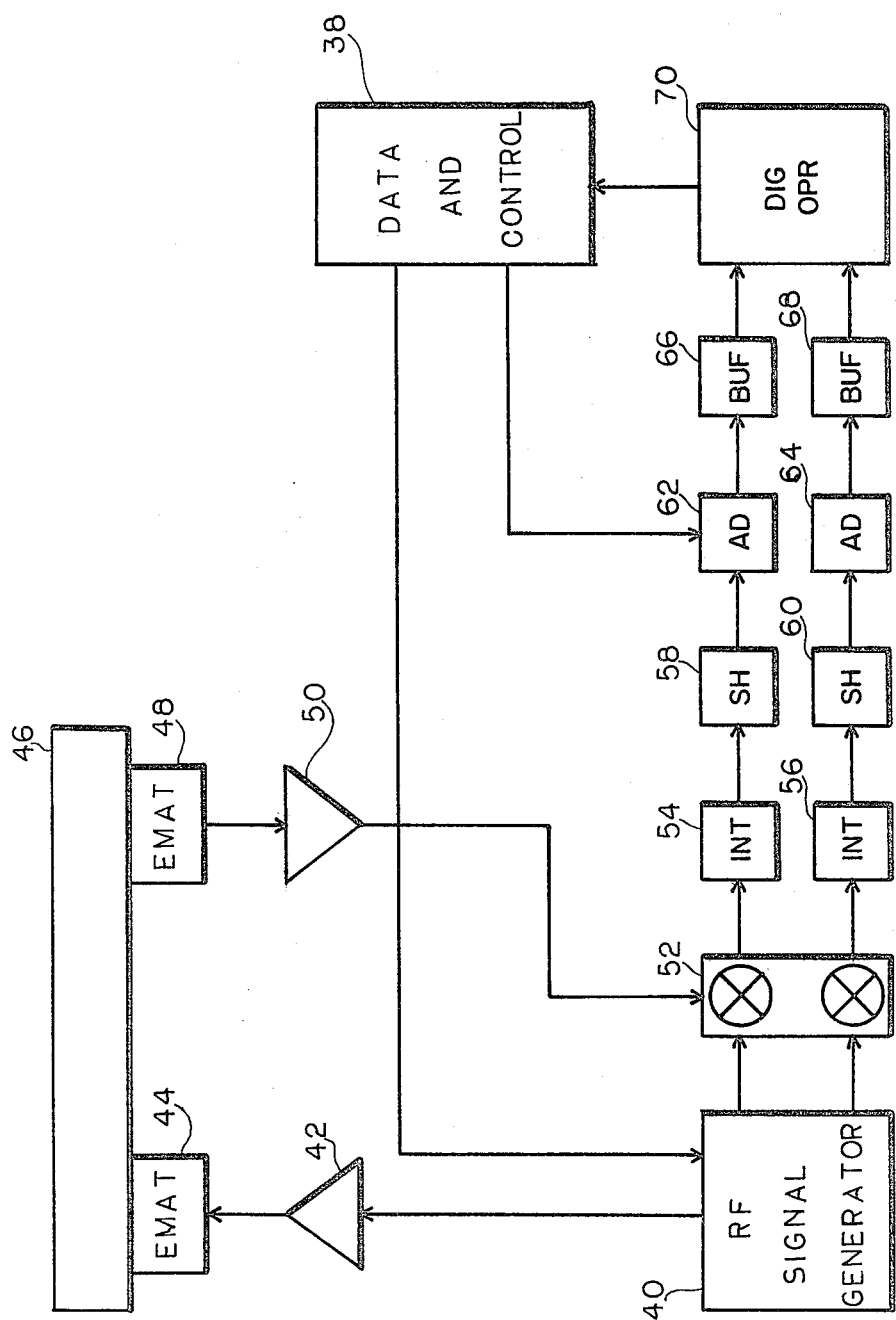
FIG. 4 is a block diagram of an ultrasonic measuring apparatus employing a second embodiment of the correlation receiver of the present invention.

A block diagram of the ultrasonic system utilized in this embodiment is illustrated in FIG. 4 The synchronous operation of the correlation receiver is digitally controlled by a central data and control processor 38, which also manages asynchronous functions, such as projectiles handling and control of the electromagnet power supplies. The processor further determines the final disposition of each projectile on the basis of received ultrasonic data and a permanently stored set of accept/reject standards.

At the beginning of each scan cycle, the processor 38 transmits an address code to a programmable RF signal generator 40. The generator 40 is internally programmed to generate a signal consisting of N cycles of an RF signal, which drives a class "C" transmitter amplifier 42. The output of the amplifier 42 in turn drives a transmitting EMAT 44, resulting in the generation of an ultrasonic signal in the adjacent portion of the projectile wall 46. The ultrasonic energy propagates in the wall 46 and is detected by a receiving EMAT 48, the output of which is boosted by a linear receiver 50, and then is applied to a multiplier 52.

After a time delay corresponding to the ultrasonic range of a resolution element within the projectile being inspected for the presence of flaws, the signal generator 40 produces two reference waveform tone bursts which are each approximately 4/3 N cycles long and are phase shifted by 90° with respect to each other. These two signals serve as reference in-phase and in-quadrature wave forms for demodulating the received ultrasonic signal after preamplification. The demodulation of the received signal is accomplished by a linear multiplication of the signal by each of the two reference wave forms. The resulting products are then integrated separately, in integrators 54 and 56, to remove second harmonic frequency components and to produce a voltage level corresponding to the signal energy in each channel.

The use of two channels is required in this application because the exact electrical phase of the ultrasonic signal scattered by a flaw cannot be accurately predicted. The outputs of the integrators are sampled individually and stored as analog voltage levels in the sample and hold circuits 58 and 60. The signals are then digitized in analog to digital converter 62 and 64, conveyed through buffers 66 and 68, and the square root of the sum of the squared integrator output signals is computed in a digital operator 70, i.e., the output of the digital operator is in the form $\sqrt{(I)^2+(Q)^2}$, where I is the integrated in-phase signal and Q is the integrated in-quadrature signal. This final operation is necessary to preserve the linearity of the detection process. The resulting quantity then is transmitted directly to the central processor 38, which compares the received data with internally stored accept/reject criteria for the purpose of determining whether a flaw has been detected.

The capability of detecting flaws in a projectile with this embodiment of the correlation receiver has been demonstrated by a prototype inspection system utilizing the correlation receiver described above. In the thicker regions of a projectile, a periodic EMAT can be used to excite and detect ultrasonic shear and longitudinal waves, with the direction of propagation of such waves determined by Snell's Law:

$$\sin \theta_{S,L} = V_{S,L}/fD \qquad (5)$$

where $\theta_{S,L}$ is the angle between the direction of propagation of the excited wave and the surface normal, V is the bulk phase velocity for shear and longitudinal waves, f is the frequency, and d is the periodicity of the transducer. This relationship is strictly obeyed only when the ultrasonic signals are excited in a thick sample, such as in the base region of a projectile, where the length of the ultrasonic tone burst is shorter than the transit time between the bounding surfaces of the part being inspected. By comparison, in the walls of a projectile, the generation and propagation properties of acoustic waves may be analyzed using a guide wave approach, i.e., as a super-position of ultrasonic wave guide modes in a finite thickness plate.

Figure 5:
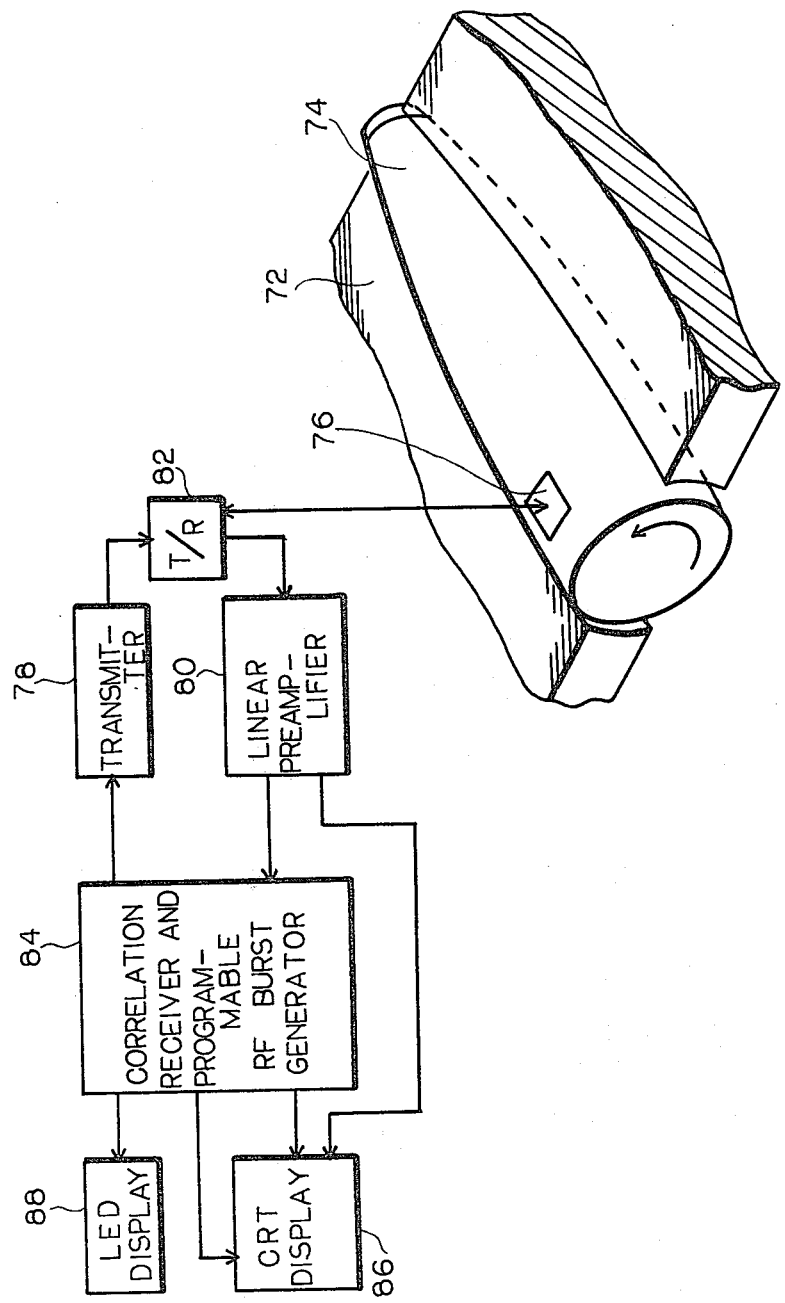
FIG. 5 is a block diagram illustrating a test configuration used in an experimental verification of the apparatus illustrated in FIG. 4, in which the apparatus was utilized to analyze an artillery projectile.

The prototype system which was utilized to demonstrate flaw detection by the correlation receiver in a projectile is illustrated in block diagram form in FIG. 5. The prototype system includes an electromagnet 72 for magnetically biasing a projectile 74 along its circumference and a single electromagnetic transducer 76 for both generating and receiving the ultrasonic signals. A transmitter 78, a linear preamplifier 80, and a transmit/receive switch 82 are provided to interface with the transducer, while a correlation receiver and programmable RF burst generator 84 function as described above. An oscilloscope 86 and an LED panel 88 were provided for displaying the received ultrasonic signals. In operation, the position and orientation of the EMAT were fixed, while the projectile was rotated about its axis of symmetry to simulate the operation of an automated test system.

The electronics package was tuned to a center frequency of approximately 1.8 MHz and the EMAT 76 was excited by a tone burst centered at this frequency and containing 8 cycles. The EMAT was configured in a meander coil geometry which contained 8 full wave periods of 0.3 cm each and had an active acoustic aperature of 2.5 cm. In addition, a 0.025 cm thick paper spacer was used as an electrical insulator and as a wear plate to maintain a constant separation from the wall of the projectile.

Two simulated defects in the projectile used for the test were produced by electron discharge machining, the first defect having a surface length of 0.95 cm and a maximum depth of 0.28 cm, while the second defect was 0.56 cm long with a depth of 0.09 cm. Both defects could be readily detected by the prototype system. The output of the correlation receiver responsive to the larger defect is indicated as a function of the separation in Table I, the output being 0.01 volts in the absence of a defect.

TABLE I

| Separation Between Transducer and Defect (Inches) | Integrator Outputs (Volts) |
|---|---|
| .75 | 1.48 |
| 1.00 | 3.70 |
| 1.25 | 3.75 |
| 1.50 | 1.72 |
| 1.75 | .77 |
| 2.00 | .24 |
| 2.25 | .13 |
| 2.50 | .01 |

In summary, the correlation receiver of the present invention offers significant advantages over the signal processing techniques of the prior art. In traditional systems, ultrasonic signals are converted to numeric flaw indications by the use of a suitably positioned gate and an adjustable level threshold detector. The peak signal-to-noise ratio of an RF signal of finite duration can be seriously degraded, however, by the filter characteristics of receiver amplifiers. In particular, it is difficult to design an amplifier for matched filtering of the triangularly shaped waveforms which are characteristic of ultrasonic inspection systems using electromagnetic transducers for the generation and reception of ultrasonic signals. The correlation receiver of this invention solves this problem by providing matched filtering through the use of time domain correlation and also exhibits a major advantage over the prior art in allowing time delay adjustments to be made electronically to compensate for variations in the propagation delays of signals in different channels. Because of this capability, a single, digitally controlled correlation receiver may be used to process the ultrasonic data from multiple ultrasonic channels. Consequently, a number of different waveforms can be demodulated, each with near optimum signal-to-noise performance, by the same device. Furthermore, the correlation receiver of this invention tends to discriminate against sharp noise pulses far better than ordinary fixed tuned receivers. For this reason, a single illumination of the resolution cell within the part under inspection wil normally suffice to discriminate against random electromagnetic interference and electrical noise generated within the signal processing system itself.

In conclusion, although typical embodiments of the present invention have been illustrated and discussed above, numerous modifications and alternative embodiments of the apparatus and method of this invention will be apparent to those skilled in the art in view of this description. Persons familiar with the uses for ultrasonic nondestructive testing, for example, may forsee many other testing environments, other than the particular testing systems discussed above, in which the correlation receiver may be advantageously utilized. Accordingly, this description should be considered as illustrative only and is provided for the purpose of teaching those skilled in the art the manner of constructing the apparatus and performing the method of this invention. Furthermore, it should be understood that the forms of the invention depicted and described herein are to be considered as the presently preferred embodiments. Various changes may be made in the configurations, sizes, and arrangements of the components of the invention, as will be recognized by those skilled in the art, without departing from the scope of the invention. Equivalent elements, for example, might be substituted for those illustrated and described herein, parts or connections might be reversed or otherwise interchanged, and certain features of the invention might be utilized independently of the use of other features, all as will be apparent to one skilled in the art after receiving the benefit obtained through reading the above description of the invention.

What is claimed is:

1. A correlation receiver for processing an electrical signal derived from an acoustic signal in a test object, comprising:
   a signal generator for producing a reference waveform;
   a multiplier for combining said electrical signal and said reference waveform; and
   an integrator for integrating the combined signal.

2. The receiver of claim 1, further comprising an amplifier for boosting the level of said electrical signal before said signal is applied to said multiplier.

3. The receiver of claim 2, further comprising a delay circuit for delaying said reference waveform so that said waveform and said electrical signal are applied to said multiplier simultaneously.

4. The receiver of claim 3, wherein:
   said reference waveform is of the form $R(t) = R_o \cos \omega_o t$ between the times $0 < t < T$ and zero elsewhere.

5. A correlation receiver for processing an electrical signal derived from an acoustic signal in a test object, comprising:
   a signal generator for producing a first reference waveform and a second reference waveform in quadrature with said first reference waveform;
   a first multiplier for combining said electrical signal and said first reference waveform;
   a second multiplier for combining said electrical signal and said second reference waveform;
   a first integrator for integrating said first combined signal;
   a second integrator for integrating said second combined signal; and
   means for combining said integrated first and second combined signals to produce an output indicating the structural integrity of the test object.

6. The receiver of claim 5, further comprising:
   a first sample and hold circuit for detecting and holding the output of said first integrator;
   a second sample and hold circuit for detecting and holding the output of said second integrator;
   a first analog to digital converter for digitizing the output of said first sample and hold circuit; and
   a second analog to digital converter for digitizing the output of said second sample and hold circuit,
   said combining means thereby being adapted to combine said integrated signals digitally.

7. The receiver of claim 6, further comprising a central data and control processor for timing the output of said first and second reference waveforms from said generator, initiating the digitization of said sample and hold outputs, making an acceptance decision regarding the test object based on the output of said combining means, and resetting the receiver.

8. The receiver of claim 7, wherein:
   said first reference waveform is of the form $R_1(t) = R_o \cos \omega_o t$ between the times $0 < t < T$ and zero elsewhere; and
   said second reference waveform is of the form $R_2(t) = R_o \sin \omega_o t$ between the times $0 < t < T$ and zero elsewhere.

9. The receiver of claim 8, wherein said combining means provides an output in the form $\sqrt{(I)^2 + (Q)^2}$, where I is said first integrated, combined signal and Q is said second integrated, combined signal.

10. An apparatus for evaluating the structural integrity of an object, comprising:
    a signal generator for producing an input signal and a reference waveform;
    an input transducer for receiving said input signal and generating an acoustic signal in the object;
    an output transducer for detecting said acoustic signal and generating an electrical output signal responsive thereto;
    a multiplier for combining said electrical output signal and said reference waveform; and
    an integrator for integrating the combined signal.

11. An apparatus for evaluating the structural integrity of an object, comprising:
    a signal generator for producing an input signal, a first reference waveform, and a second reference waveform;
    an input transducer for receiving said input signal and generating an acoustic signal in the object;
    an output transducer for detecting said acoustic signal and generating an electrical output signal responsive thereto;
    a first multiplier for combining said electrical output signal and said first reference waveform;
    a second multiplier for combining said electrical output signal and said second reference waveform;
    a first integrator for integrating said first combined signal;
    a second integrator for integrating said second combined signal; and means for combining said integrated signals to produce an output indicating the structural integrity of the test object.

12. A method of time domain correlating an electrical signal derived from an acoustic signal in a test object, comprising the steps of:
(a) generating a first reference waveform;
(b) combining the electrical signal and the reference waveform by multiplication; and
(c) integrating the product of the multiplication.

13. The method of claim 12, further comprising the steps of:
(d) generating a second reference waveform in quadrature with the first waveform;
(e) combining the electrical signal and the second reference waveform by multiplication;
(f) integrating the product of the multiplication; and
(g) combining the integrands from steps (c) and (f) to provide an output indicating the structural integrity of the test object.

* * * * *